United States Patent [19]

Maruyama et al.

[11] 4,233,257
[45] Nov. 11, 1980

[54] METHOD OF MAKING A LIQUID JUNCTION FOR A REFERENCE ELECTRODE

[75] Inventors: Hiroshi Maruyama; Masashi Watanabe, both of Kyoto, Japan

[73] Assignee: Horiba, Ltd., Kyoto, Japan

[21] Appl. No.: 902,836

[22] Filed: May 2, 1978

Related U.S. Application Data

[62] Division of Ser. No. 705,284, Jul. 14, 1976, abandoned.

[30] Foreign Application Priority Data

Jul. 14, 1975 [JP] Japan ................................ 50-85944

[51] Int. Cl.³ .......................... B29F 5/02; G01N 27/30
[52] U.S. Cl. ................................. 264/113; 204/195 F; 264/127
[58] Field of Search ..................... 204/195 F; 264/113, 264/127, 154

[56] References Cited

U.S. PATENT DOCUMENTS

| | | | |
|---|---|---|---|
| 2,710,991 | 6/1955 | Barrington et al. | 264/113 |
| 2,951,721 | 9/1960 | Asp | 264/127 |
| 3,000,804 | 9/1961 | Cahoon et al. | 204/195 F |
| 3,208,927 | 9/1965 | Arthur et al. | 204/195 F |
| 3,385,780 | 5/1968 | Feng | 264/127 |
| 3,389,017 | 6/1968 | Webb | 264/113 |
| 3,575,834 | 4/1971 | Hoole et al. | 204/195 F |
| 3,723,589 | 3/1973 | Kennedy | 264/113 |
| 3,840,631 | 10/1974 | Alexander | 264/113 |
| 3,843,506 | 10/1974 | Jerrold-Jones | 204/195 F |
| 4,002,547 | 1/1977 | Neti et al. | 204/195 F |
| 4,102,966 | 7/1978 | Duperray et al. | 264/113 |

*Primary Examiner*—G. L. Kaplan
*Attorney, Agent, or Firm*—Wenderoth, Lind & Ponack

[57] ABSTRACT

A liquid junction for a reference electrode and a method of forming the same, in which a hydrophobic polymer support material has a liquid junction layer or portion of material therein comprised of a hydrophobic polymer in mixture with either an inactive particulate substance, an electro-chemically inactive salt, or a combination of said inactive particulate substance and said electro-chemically inactive salt. The support member and the liquid junction therein are compression formed in a mold and are heat-treated following the final compression treatment.

6 Claims, 15 Drawing Figures

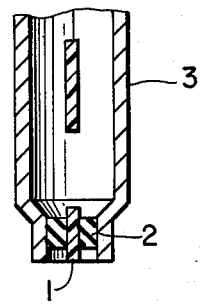
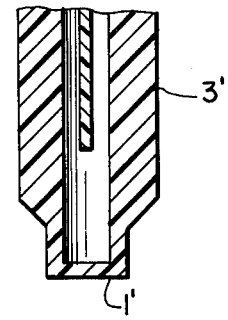
FIG. 1    FIG. 2
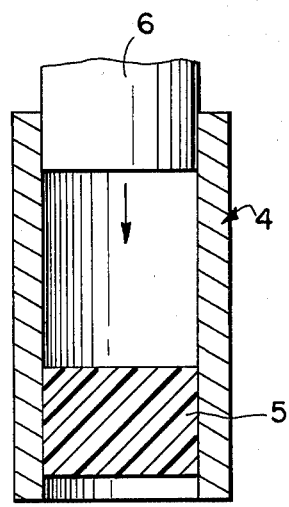
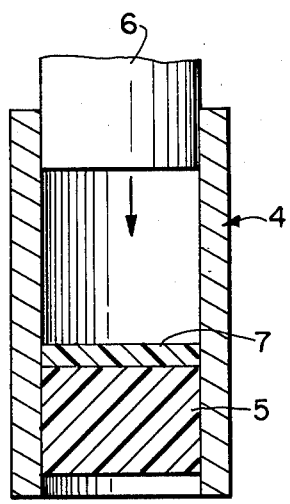
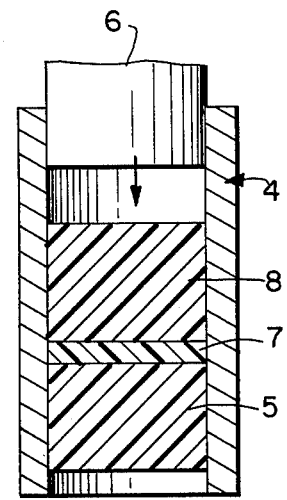
FIG. 3A    FIG. 3B    FIG. 3C

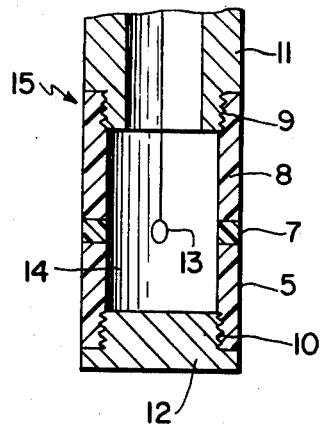
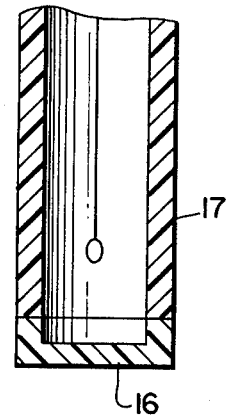
FIG. 4  FIG. 5
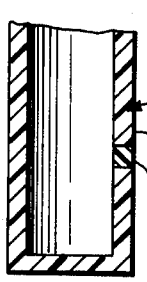
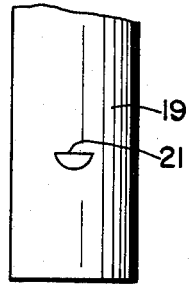
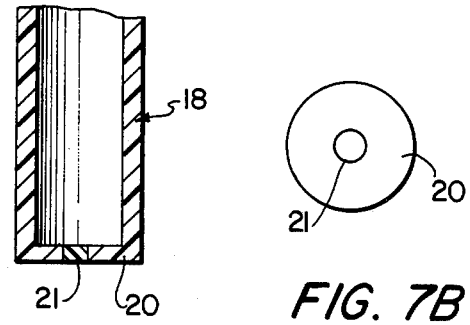
FIG. 6A  FIG. 6B  FIG. 7A  FIG. 7B
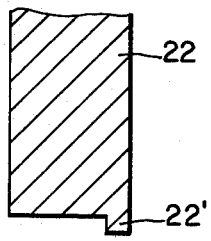
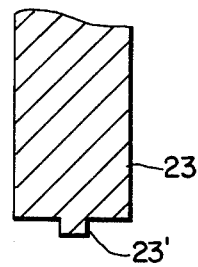
FIG. 8A  FIG. 9A
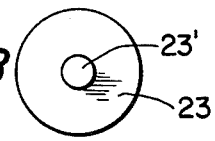
FIG. 8B  FIG. 9B

METHOD OF MAKING A LIQUID JUNCTION FOR A REFERENCE ELECTRODE

This application is a division of application Ser. No. 705,284, filed July 14, 1976 and now abandoned.

The present invention relates to a liquid junction of a reference electrode for measuring the ionic concentration of a solution and, especially, relates to a liquid junction prepared by using a hydrophobic polymer such as polytetrafluoroethylene (Teflon).

BACKGROUND OF THE INVENTION

Examples of liquid junctions for reference electrodes are shown in FIG. 1 and FIG. 2. In these examples, a liquid junction of plate or rod shape consists of Teflon and is fixed to a supporter 3 with a rubber packing or a binder 2 (FIG. 1), or a liquid junction 1' is prepared, after molding a polymer of tetrafluoroethylene mixed with potassium chloride under a pressure and sintering it, by scraping a portion of the molded product into a thinner layer to reduce its electrical resistance (FIG. 2).

However, in the case of the electrode of FIG. 1, sometimes problems arise with respect to the chemical stability of the rubber packing or the binder to the solution which is to have its ionic concentration measured, and moreover problems arise regarding the thermal stability of the rubber packing or the binder. In the case of the electrode of FIG. 2, it is rather difficult to make a portion of the molded polymer into the thinner layer and moreover, there is a possibility of introducing error into the measurement of the ionic concentration of a solution by the appearance of an electric potential difference between an internal liquor and the solution in the region of a thicker portion 3' in FIG. 2, since the absorption of the solution to be measured by the thicker portion 3' cannot necessarily be neglected under all conditions.

SUMMARY OF THE INVENTION

The present invention provides a liquid junction of reference electrode, which is very easy to prepare and at the same time, scarcely generates any liquid - liquid potential difference, creates no trouble in regard to being reagent-proof, and also is antithermal, thereby overcoming the defects experienced in the conventional liquid junctions mentioned above.

The invention is essentially a hydrophobic polymer support material having a liquid junction layer or portion of material therein comprised of a hydrophobic polymer in mixture with either an inactive particulate substance, an electrochemically inactive salt, or a combination of said inactive particulate substance and said electro-chemically inactive salt. The support member and the liquid junction therein are compression formed in a mold and are heat-treated following the final compression treatment.

BRIEF DESCRIPTION OF THE DRAWINGS

Further objects of the present invention will be apparent from the formal drawings, wherein:

FIG. 1 and FIG. 2 are vertical sectional views of conventional reference electrodes;

FIGS. 3(a), 3(b) and 3(c) are vertical sectional views of a metallic mold as embodied in the present invention;

FIG. 4 is a vertical sectional view of a reference electrode of the present invention having a liquid junction;

FIG. 5 is also a vertical sectional view of a reference electrode of the present invention having another type of liquid junction;

FIGS. 6(a) and 6(b) are, respectively, a vertical sectional view and a front view of other embodiment of the present invention showing how to realize the invention;

FIGS. 7(a) and 7(b) are, respectively, a vertical view and a cross sectional view of another embodiment of a liquid junction of the present invention; and FIGS. 8(a), 8(b), 9(a) and 9(b) are, respectively, vertical views and views of base surfaces of other embodiments of the metallic molds of the present invention.

DETAILED DESCRIPTION OF THE PREFERRED EMBODIMENT

In the following, the invention is explained in detail with reference to the attached drawings.

FIGS. 3(a), 3(b) and 3(c) show a metallic mold 4 of cylindrical shape, into which a proper amount of hydrophobic polymer 5, such as polytetrafluoroethylene, in powder form or granular form is charged (FIG. 3(a)). (It should, however, be noted that a polymer used in the present invention is not necessarily limited to be polytetrafluoroethylene.) After compressing the polymer under a small pressure using a metallic piston rod 6, a proper amount of any one of the following mixtures 7 is charged into the mold 4 as shown in FIG. 3(b). These mixtures may be:

(A) a mixture of polytetrafluoroethylene in powder form or granular form and an inactive particulate substance, state such as glass powder, asbestos and carbon, etc.;

(B) a mixture of polytetrafluoroethylene in powder form or granular form and an electro-chemically inactive salt, such as potassium chloride, sodium chloride, etc.; and (C) a mixture of polytetrafluoroethylene in powder form or of granular form, said inactive substance in particulate form and said electro-chemically inactive salt.

Finally, after compressing the contents in the mold with a small pressure, a proper amount of polytetrafluoroethylene is charged into the mold 4 to make the third layer 8 as shown in FIG. 3(c). Now, the contents are compressed with a strong pressure using the piston rod 6 (for example, approximately 600kg/cm$^2$ is applied when polytetrafluorethylene is used). The molded substance containing the liquid junction 7 prepared as mentioned above, is treated thermally in a sintering oven. The temperature for the thermal treatment in the oven is, for example, preferably in the range of 350° C. to 390° C. when polytetrafluoroethylene is used, and the treating time is about 2 hours when the diameter of the moulded polytetrafluoroethylene is 20 mm. By the thermal treatment, the liquid junction 7 and the two supporting layers 5 and 8, (wherein between the liquid junction 7 is sandwiched) form one complete body since they consist essentially of a common polymerized material. The thermally treated polytetrafluoroethylene can be easily worked to make it into the liquid junction 7 and the supporters 5 and 8 of the reference electrode of the present invention, as shown in FIG. 4, by hollowing the central portion of the rod, by preparing screws 9 and 10 around the inside peripheries at both ends of the hollow rod and by providing supporters 11 and 12, an internal electrode 13 and an internal liquor 14.

Next, FIG. 5 shows another embodiment of the present invention which is different from that shown in FIG. 4 wherein, as stated already, a ring-shaped liquid junction is inserted between two supporters 10, 11. In FIG. 5, a rod, consisting of a layer of liquid junction 16 and a layer of supporter 17, is, also prepared in a metallic mold. A proper amount of any one of the said material mixtures (A), (B) and (C) for the liquid junction 17 is charged into said mold under a weak pressure and then, a proper amount of polytetrafluoroethylene in powder form or granular form is charged on the first layer 17 and molded under a stronger pressure, and, at last, a thermal treatment is carried in a sintering oven to bind the two layers tightly into one body. The thermally treated rod can be worked easily to prepare the reference electrode of the present invention as shown in FIG. 5. Furthermore, the liquid junction of the present invention shown in FIG. 6(a) and 6(b) or in FIG. 7 (a) and 7(b) can be easily prepared wherein, in FIG. 6, a liquid junction 21 is provided only at a portion of the peripheral side wall 19 of a supporter 18 and in FIG. 7, a liquid junction 21 is provided only at a portion of the bottom 20 of a supporter 18. In these embodiments, the liquid junctions can be prepared by compression molding using a metallic mold as shown in FIG. 8(a) and 8(b) in the former case or a metallic mold as shown in FIG. 9(a) and 9(b) in the latter case. Upon compressing the polytetrafluoroethylene in these molds under a weak pressure by a piston rod 22 or 23 having a projection 22′ or 23′, a depression or a cavity corresponding to the type and shape of the projection 22′ or 23′ is first prepared, then the depression or the cavity prepared in the polytetrafluoroethylene layer is filled with the said material mixture for the liquid junction. Further, a proper amount of polytetrafluoroethylene is added onto the liquid junction and is finally molded under a strong pressure and receives a thermal treating to make a rod. By scraping the obtained rod into a desired configuration, the liquid junction shown in FIG. 6 or 7 can be produced.

Various types of molds and piston rods other than those mentioned above can be used to practice the present invention. Moreover, it should be pointed out that by the choice of a proper mold and an appropriate piston rod, it is possible to produce a liquid junction part with a supporter part only by molding and thermal treating, without any mechanical work such as scraping.

As the characteristic feature of the present invention, the following advantages can be pointed out. Since the liquid junction of the reference electrode of the present invention is constructed with a liquid junction part and since its supporter part is combined tightly into a body chemcially, physically, and also mechanically, as explained in above, the omission of the liquid junction part from the supporter part will never happen. Furthermore, since there exists no necessity for using rubber packing or binder as in the conventional liquid junction, any troublesome problems with respect to the attachment of the liquid junction part to the supporter part (for example, such problems as resistance to chemical reagents and thermal stability) of the packing and the binder never arise. The liquid junction of any desired figure and dimension is easily made at any desired position of the supporter as explained above, and it is pointed out that, generally, the production of a liquid junction of the present invention is much easier than that by any conventional technique. Furthermore, it is easily possible to prepare a very small liquid junction part. Moreover, no error arises from the generation of the liquid - liquid potential differences in the region of the supporter such as has already been explained in light of the conventional liquid junction shown in FIG. 2.

What is claimed is:

1. A method of forming a liquid junction for a reference electrode comprising:
   forming a first support layer of polytetrafluoroethylene alone in a mold;
   compressing said first support layer;
   forming a second liquid junction layer on top of said compressed first layer, said second layer comprising one material selected from the group consisting of:
   a mixture of a polytetrafluoroethylene and an inactive particulate substance
   a mixture of polytetrafluoroethylene and an electro-chemically inactive salt, and
   a mixture of polytetrafluoroethylene, an inactive particulate substance, and an electro-chemically inactive salt;
   compressing said second liquid junction layer;
   forming a third support layer of polytetrafluoroethylene alone on top of said compressed second liquid junction layer;
   compressing said third support layer; and
   sintering said three compressed layers.

2. A method as claimed in claim 1, further comprising forming a longitudinal opening completely through said three layers.

3. A method as claimed in claim 1, wherein:
   said inactive particulate substance is selected from the group consisting of glass powder, asbestos, and carbon; and
   said electro-chemically active salts are selected from the group consisting of potassium chloride and sodium chloride.

4. A method according to claim 1 wherein the first support layer is formed using weak pressure by a piston rod which forms a depression or cavity corresponding to a desired shape, the depression or cavity is then filled with the material for the said second layer and said material is compressed, the third support layer is then formed and the entire unit is molded under strong pressure and subjected to sintering.

5. A method according to claim 4, wherein the strong pressure is about 600 Kg/cm$^2$.

6. A method according to claim 1 wherein the sintering is at a temperature of 350° C. to 390° C.

* * * * *